(12) United States Patent
Lafosse et al.

(10) Patent No.: US 8,585,706 B2
(45) Date of Patent: Nov. 19, 2013

(54) INSTRUMENT FOR USE IN A JOINT REPLACEMENT PROCEDURE

(75) Inventors: Laurent Lafosse, Sevrier (FR); Julien Hee, Lyons (FR); Didier Poncet, Bron (FR)

(73) Assignee: Depuy (Ireland) (IE)

( * ) Notice: Subject to any disclaimer, the term of this patent is extended or adjusted under 35 U.S.C. 154(b) by 1465 days.

(21) Appl. No.: 11/916,412

(22) PCT Filed: Jun. 2, 2006

(86) PCT No.: PCT/IB2006/002189
§ 371 (c)(1),
(2), (4) Date: Aug. 14, 2008

(87) PCT Pub. No.: WO2006/136955
PCT Pub. Date: Dec. 28, 2006

(65) Prior Publication Data
US 2009/0222010 A1 Sep. 3, 2009

(30) Foreign Application Priority Data
Jun. 3, 2005 (GB) .................................. 0511292.5
Feb. 22, 2006 (GB) .................................. 0603471.4

(51) Int. Cl.
*A61F 5/00* (2006.01)
(52) U.S. Cl.
USPC ........................................................ 606/87
(58) Field of Classification Search
USPC .................... 606/86 R, 87–89, 96–98, 102
See application file for complete search history.

(56) References Cited

U.S. PATENT DOCUMENTS

| 4,893,619 | A | * | 1/1990 | Dale et al. .................... 606/87 |
| 5,070,623 | A | | 12/1991 | Barnes |
| 5,364,401 | A | * | 11/1994 | Ferrante et al. .............. 606/84 |

(Continued)

FOREIGN PATENT DOCUMENTS

| DE | 10123517 C1 | 11/2002 |
| EP | 0712617 A1 | 5/1996 |

(Continued)

OTHER PUBLICATIONS

U.S. Appl. No. 11/916,403, filed Sep. 5, 2008; Non-Final Rejection Aug. 6, 2009; Final Rejection Apr. 14, 2010.

(Continued)

*Primary Examiner* — Kevin T Truong
*Assistant Examiner* — Christopher Beccia

(57) ABSTRACT

An instrument for locating the cutting plane on the head of a long bone in a surgical procedure, wherein the head of the bone is replaced with a joint prosthesis component, includes an axial reference shaft which can be arranged parallel to the axis of the bone and a cutting guide which can be moved relative to the axial reference shaft. The cutting guide has a reference block for location against the bone relative to the edge of the bone at one side and at least one arm which is shaped so that it can extend from the cutting guide over the face of the head. The arm can be located positively with respect to features on the head so that the location of the reference block along the axis of the bone can be set with reference to features on the head of the bone which are contacted by means of the arm.

19 Claims, 3 Drawing Sheets

(56) References Cited

U.S. PATENT DOCUMENTS

| | | | |
|---|---|---|---|
| 5,397,330 A | 3/1995 | Mikhail | |
| 5,462,549 A | 10/1995 | Glock | |
| 5,496,323 A | 3/1996 | Dye | |
| 5,514,139 A * | 5/1996 | Goldstein et al. | 606/79 |
| 5,571,203 A | 11/1996 | Masini | |
| 5,578,037 A * | 11/1996 | Sanders et al. | 606/80 |
| 5,683,397 A | 11/1997 | Vendrely | |
| 5,704,941 A * | 1/1998 | Jacober et al. | 606/88 |
| 5,779,709 A * | 7/1998 | Harris et al. | 606/87 |
| 5,800,437 A | 9/1998 | Gustilo | |
| 6,203,575 B1 | 3/2001 | Farey | |
| 6,258,097 B1 | 7/2001 | Cook | |
| 6,503,255 B1 * | 1/2003 | Albrektsson et al. | 606/89 |
| 6,575,980 B1 * | 6/2003 | Robie et al. | 606/88 |
| 6,589,282 B2 | 7/2003 | Pearl | |
| 6,712,823 B2 * | 3/2004 | Grusin et al. | 606/87 |
| 6,783,549 B1 | 8/2004 | Stone | |
| 7,198,628 B2 * | 4/2007 | Ondrla et al. | 606/87 |
| 7,618,421 B2 * | 11/2009 | Axelson et al. | 606/88 |
| 7,931,655 B2 * | 4/2011 | Axelson et al. | 606/88 |
| 8,197,487 B2 * | 6/2012 | Poncet et al. | 606/87 |
| 8,226,658 B2 * | 7/2012 | Anthony et al. | 606/87 |
| 2002/0072805 A1 | 6/2002 | Sullivan et al. | |
| 2002/0099381 A1 * | 7/2002 | Maroney | 606/86 |
| 2003/0009170 A1 * | 1/2003 | Tornier | 606/87 |
| 2003/0114859 A1 * | 6/2003 | Grusin et al. | 606/87 |
| 2004/0064187 A1 | 4/2004 | Ball | |
| 2004/0162619 A1 | 8/2004 | Blaylock | |
| 2004/0186579 A1 | 9/2004 | Callaway et al. | |
| 2004/0215205 A1 | 10/2004 | Plumet | |
| 2004/0236341 A1 * | 11/2004 | Petersen | 606/89 |
| 2006/0004373 A1 * | 1/2006 | Ondrla et al. | 606/87 |

FOREIGN PATENT DOCUMENTS

| | | |
|---|---|---|
| EP | 1523964 A2 | 4/2005 |
| FR | 2773469 A1 | 7/1999 |
| FR | 2863859 A1 | 6/2005 |
| GB | 1448111 A | 9/1976 |
| WO | WO 94/15551 A | 7/1994 |
| WO | WO 9415551 A1 | 7/1994 |
| WO | WO 96/36284 A | 11/1996 |
| WO | WO 9636284 A1 | 11/1996 |
| WO | WO 99/15084 | 4/1999 |
| WO | WO 9915084 A1 | 4/1999 |
| WO | WO 02/17822 A1 | 3/2002 |
| WO | WO 0217822 A1 | 3/2002 |
| WO | WO 02/26145 A | 4/2002 |
| WO | WO 0226145 A1 | 4/2002 |
| WO | WO 03094803 A1 | 11/2003 |

OTHER PUBLICATIONS

U.S. Appl. No. 11/916,415, filed Nov. 19, 2008; Non-Final Rejection May 14, 2010.
PCT Written Opinion, 6 pages.
International Search Report, dated Oct. 11, 2006, 6pages.
UK Search Report, dated Oct. 4, 2005, 1 page.
UK Search Report, dated May 22, 2006, 1 page.

* cited by examiner

INSTRUMENT FOR USE IN A JOINT REPLACEMENT PROCEDURE

CROSS REFERENCE TO RELATED APPLICATION

This application is a National Stage 35 U.S.C. 371 of International Patent Application PCT/IB2006/002189 filed Jun. 2, 2006.

This invention relates to an instrument for use in a procedure for implanting an joint prosthesis in a joint between a long bone and another bone.

It is desirable to minimise the size of an incision through which a joint replacement procedure is performed. This can help to reduce the time taken for a patient to recover. When access to tissue for visual inspection is restricted because of the small size of an incision, it can be necessary to rely on instruments to locate tissue components, for example for the purpose of identifying a resection plane.

Commonly used techniques for shoulder joint replacement involve making an anterior incision. The deltoid muscle is split and so that the joint can be dislocated. The incision that is required to perform these steps enables the humeral head to be inspected visually to identify the appropriate location of the plane on which it is to be resected.

The present invention provides instruments which can be used in joint replacement procedures using a lateral approach. The use of a supero-lateral approach can have advantage of reducing soft tissue damage, and possibly also allowing a smaller incision to be used.

Accordingly, in one aspect, the invention provides an instrument for locating the cutting plane on the head of a long bone in a surgical procedure in which the head of the bone is replaced with a joint prosthesis component, which includes an axial reference shaft which can be arranged parallel to the axis of the bone, a cutting guide which can be moved relative to the axial reference shaft, the cutting guide having a reference block for location against the bone relative to the edge of the bone at one side and at least one arm which is shaped so that it can extend from the cutting guide over the face of the head, in which the arm can be located positively with respect to features on the head so that the location of the reference block along the axis of the bone can be set with reference to features on the head of the bone which are contacted by means of the arm.

In another aspect, the invention provides a method of resecting the head of a long bone in a joint replacement procedure, which includes the steps of:
  locating an instrument which includes an axial reference shaft relative to the long bone so that the shaft extends parallel to the axis of the bone,
  moving a cutting guide relative to the axial reference shaft, the cutting guide having a reference block for location against the bone relative to the lateral edge of the bone and at least one arm which is shaped so that it can extend from the cutting guide over the superior face of the head, so that the arm is located positively with respect to features on the head and so that the location of the reference block along the axis of the bone is set with reference to features on the head of the bone which are contacted by means of the arm.

The invention can enable the plane for resection of a bone to be located with reference to features of the bone which are not available for visual inspection. This can be important when the features which are visible through the incision do not enable the position of the resection plane to be defined reliably so that its position should preferably be determined with reference to other features. In particular, when the bone is a humerus which is to be resected for the purposes of implantation of a humeral component of a shoulder joint prosthesis, it can be preferable to locate the resection plane with reference to the superior surface of the humeral head, or to the lip at the medial edge of the head, or to both. Access to the superior surface and to the medial edge of the humeral head for visual inspection can be restricted when the procedure is performed through a superior-lateral incision. The instrument of the invention therefore facilitates the performance of a shoulder joint replacement through a superior-lateral incision. Such a procedure has the advantage that it avoids the need to release the subscapularis. It can therefore eliminate the risk of post-operative rupture of the subscapularis which can be associated with the known anterior approach through deltopectoral tissue. Furthermore, the size of a superior-lateral incision that is necessary to perform the procedure is smaller than is needed for the anterior approach. For example, the procedure which is contemplated using the instrument of the present invention might be performed through an incision whose length is as little as 6 cm or less. Accordingly, the technique that is facilitated by the component of the invention can help to reduce patient recovery time.

A further advantage of a shoulder joint procedure which is performed through a supero-lateral incision is that easier access to the glenoid is available compared with the known anterior approach through deltopectoral tissue, even when the size of the supero-lateral incision is small.

The location of the reference block along the axis of the bone can be set with reference to the superior surface of the bone by appropriately setting the distance parallel to the axis of the bone between the reference block and the arm. For the purpose of the subsequent resection step of the procedure, the reference block defines a plane. Preferably, the arm includes an approximately straight portion which extends from the cutting guide towards the opposite side of the bone, approximately parallel to the intended resection plane of the bone. The distance between the arm and the intended resection plane can then correspond to the size of the implant.

The arm will generally extend from the side of the bone at which the cutting guide is provided, over the head of the bone, to contact features of the bone on the side of the bone which is opposite to the side on which the cutting guide is provided.

Accordingly, in another aspect, the invention provides a kit for use in a procedure for replacement of the head of a long bone in a joint replacement procedure, which comprises an instrument as claimed in any one of the preceding claims, and a head component having an external surface in the form of part of a sphere which is truncated on a head component plane, in which the reference block defines a reference block plane and the arm defines an arm plane which is parallel to the reference block plane, and in which the distance between the reference block plane and the arm plane is approximately equal to the distance between the pole of the head component and the head component plane.

The head component of the kit can be a trial head or it can be a part of the prosthesis which is to be implanted in the patient.

Preferably, the arm has a lip which can be fitted over an edge of the head of a bone, within a joint space, especially an edge which is opposite to the side of the bone through which access is gained to the joint space. For example, the lip on the bone can be fitted over the medial-lateral edge of the head of a humerus during a procedure which is performed through a supero-lateral incision. The lip can be provided at the end of the arm. Engagement of the lip over the edge of the head of the bone can be used to locate the arm (and therefore also the reference block) relative to the head along the axis of the bone. Engagement of the lip with the bone can also be used to help to restrict relative movement between the arm and the bone, especially when the lip is sufficiently sharp to penetrate the surface of the bone tissue. Preferably, the arm engages the cutting guide in a sliding arrangement such that the arm can be slid along its length in the cutting guide. This can allow the lip on the arm to be drawn towards the surface of the bone on its medial side, so as to penetrate the surface of the bone.

When the arm has a lip which can be fitted over the edge of the head of a bone it can be used to gauge the size of the head of the bone. For example, when the arm has a lip at or towards its free end, and a straight portion extending towards the cutting guide the distance between the free end and the straight portion measured perpendicular to the straight portion provides an indication of the depth of the head, which can be important when selecting an appropriately sized head part of the joint prosthesis component.

Preferably, the arm and the reference block can be moved together relative to the axial reference shaft. It can be preferred for the spacing between the arm and the reference block (measured parallel to the axis of the bone) to be adjustable according to the desired depth of bone which is to be resected from the end of the bone. For example, the arm can engage the cutting guide in a sliding arrangement by means of a clamp (for example using a threaded screw) which, when released, allows the arm to slide along the cutting guide in a direction which is parallel to the bone axis.

Preferably, the instrument includes a second arm which, like the first arm, is shaped so that it can extend from the cutting guide over the superior face of the head of the bone. For example, the first and second arms can be located so that they can be located one on each side of the instrument component which defines the intramedullary axis.

Preferably, the instrument of the invention includes an intramedullary element which can be fitted into the intramedullary cavity within the bone to determine the axis of the bone. For example, the intramedullary element can be a reamer. Preferably, the instrument includes a transverse reference shaft which can be clamped to the intramedullary element and can extend transversely from the intramedullary element to be engaged by the cutting guide. The transverse reference shaft can move with the cutting guide parallel to the bone axis. The transverse reference shaft can be fixed relative to the intramedullary element so that the cutting guide moves relative to the transverse reference shaft parallel to the bone axis.

The instrument of the invention can include a clamp for restricting movement of the cutting guide relative to the axial reference shaft.

The reference block can be used define the orientation of the plane relative to the axis of the bone. Preferably, the reference block has features which lie in or parallel to the intended cutting plane. For example, the reference block can have a surface which is used to guide the blade of a cutting tool (especially a saw) in the resection step. The reference block might have bores formed in it to define the locations of holes in the bone to fasten a separate resection guide block. The reference surface can define a slot which can be used to guide the blade of a cutting tool (especially a saw) in the resection step.

The component of the invention can be used in procedures to replace components of various joint, including for example shoulder, elbow, wrist, hip, knee and ankle joints. The component is particularly well suited for use in procedures to replace hip and shoulder joints, in particular to determine the plane for resecting the head of the humerus or the femur.

Initial steps of a surgical procedure to replace the head of a long bone can include:
making an incision,
locating a plane on which to resect the long bone to remove the head,
performing a resection to remove the head of the bone,
preparing the cavity within the resected bone to receive the trial implant component, and
subsequently the implant component of the joint prosthesis.

More particularly, it is preferred that the procedure includes the steps of:
using a trial disk to determine the relevant width of the resected bone so that an implant with an appropriate transverse size (which will be a diameter when the implant is circular) is selected,
using a cutting guide to determine the height of the resected head of the bone so that an implant with the appropriate height is selected, and
using a trial head component to assess soft tissue balance during articulation of the joint.

Subsequent steps can include final preparation of the joint prosthesis component and implantation thereof.

The intended location of moving parts of the cutting guide can be determined as a result of pre-operative planning steps, in which the shape and size of the bone into which it is to be implanted are assessed by appropriate imaging techniques. Components of the instrument of the invention, including in particular the reference block, can be provided with features which enable its location (including orientation) to be tracked remotely, for example using magnetic tracking apparatus. Such apparatus, and components which can be included in surgical instruments such as the instrument of the present invention are known. This can enable, for example, the location and orientation of the reference block to be monitored.

It can be preferable to use a low profile trial implant component to facilitate insertion of the trial implant component into the joint space through a small incision.

The cavity within the long bone can be prepared using appropriate tools. Such tools might include drills, reamers, broaches and rasps, as is generally known.

In another aspect, the invention provides a method for a superolateral approach minimally invasive shoulder arthroplasty surgical procedure. The procedure can comprise some or all of the following: making an incision in the deltoid muscle along the direction of the deltoid fibres; splitting the deltoid muscle along its fibres; removing the glenohumeral ligaments and the coracoacromial ligament and releasing the biceps tendon; resecting the humeral head using a cutting guide; using a broach tool to provide a cavity within the humerus; using a trial stem inserted in the cavity to determine the size of a stem implant; using a trial head to determine the size of a head implant by engaging the trial head with a trial stem in the humerus; and implanting a stem implant and head implant having the determined sizes, and any combination thereof.

As the method uses an incision through the deltoid muscle to gain access to the surgical site, the rotator cuff muscles, and in particular the subscapularis, are not affected, damaged or cut during the procedure. As a result, the risk of post-operation complications for the patient are reduced. The method also has a number of other advantages. The method provides a reduced patient recovery time, a reduced risk of the patient suffering from a ruptured subscapularis, a reduced risk of weakening the shoulder joint and a reduced risk of limiting the movement of the shoulder.

The incision is made in the direction of the deltoid fibres. Preferably, the incision is made substantially vertically. Preferably, the deltoid is split in the direction of the fibres and therefore the deltoid is not damaged during this procedure. After making an incision through the deltoid muscle a further incision is made through the cuff muscle. Preferably, the incision through the cuff muscle is made between the supraspinatus and the subscapularis. The present invention therefore has the advantage that the cuff muscles, in particular the subscapularis are not damaged during the procedure. The recovery time of the patient undergoing the surgical method of the present invention compared to the recovery time of a patient undergoing conventional methods can be significantly reduced.

The instrument of the invention can be made from materials such as are commonly used in the manufacture of surgical instruments, especially from metallic materials. Preferred examples might include certain stainless steels.

Embodiments of the invention will now be described by way of example with reference to the accompanying drawings, in which.

Figure 1:
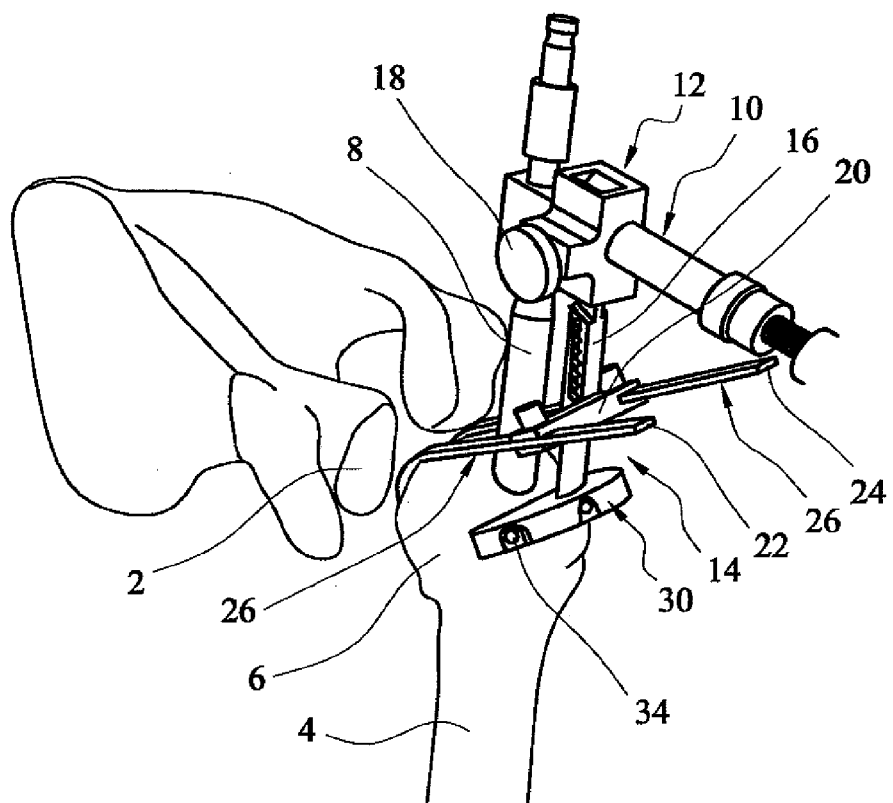
FIG. 1 is an isometric view of the anterior-lateral aspect of an exploded shoulder joint, with the instrument of the invention mounted on the humerus.

Referring to the drawings, FIG. 1 shows the skeletal structures of a shoulder joint, which includes a glenoid 2, and a humerus 4 having a humerus head 6 which can articulate with the glenoid. Access is gained to the joint through an superior-lateral incision in the deltoid muscle along the direction of the deltoid fibres. The glenohumeral ligaments and the coracoacromial ligament are removed, allowing the biceps tendon to be released. The deltoid muscle is split along its fibres.

The intramedullary cavity is located and prepared for receiving an intramedullary implant using a reamer instrument 8.

A transverse arm 10 is clamped to the reamer instrument. A suitable clamp might include a collar which can extend around the reamer instrument, and be closed around it by means of a threaded fastener. The transverse arm has a channel 12 formed in it.

A cutting guide 14 includes a shaft 16 which can pass through the channel 12 in the transverse arm 10. A screw 18 with a knurled head which is threadingly engaged in an opening in the wall of the transverse arm 10 can be used to engage a face of the shaft to lock it against movement in the channel relative to the arm.

The cutting guide 14 includes a mounting block 20 for first and second guide arms 22, 24, which can slide through the mounting block. Each of the guide arms has a generally straight portion 26 extending from the mounting block, and is curved towards its free end, ending in a in-turned lip 28. The guide arms can be locked against sliding through the mounting block by means of an appropriate clamp, for example a screw 29 which can act against a surface of its respective arm.

The cutting guide 14 includes a reference block 30 at its lower end. The reference block is fixed relative to the shaft 16. The reference block has an upper surface 32 which is approximately parallel to the straight portions 26 of the guide arms 22, 24. The distance between the upper surface of the reference block and the lower surface of the guide arms (which faces towards the reference block) is selected so that it is the same as the height of the head part of the humeral component of a shoulder joint prosthesis which is to be implanted. That distance might be adjustable so that the instrument can be used to prepare a humerus to receive head parts with a range of different heights. When the head part has the external shape of a truncated sphere, its height is measured from the pole to the plane on which it has been truncated. The height of typical head parts of a humeral component of a shoulder joint prosthesis can vary from about 15 mm to about 21 mm. The height should preferably match as closely as possible the height of the natural head of the resected humerus.

The reference block 30 has three guide holes 34 extending through it, parallel to the upper surface 32.

Figure 2:
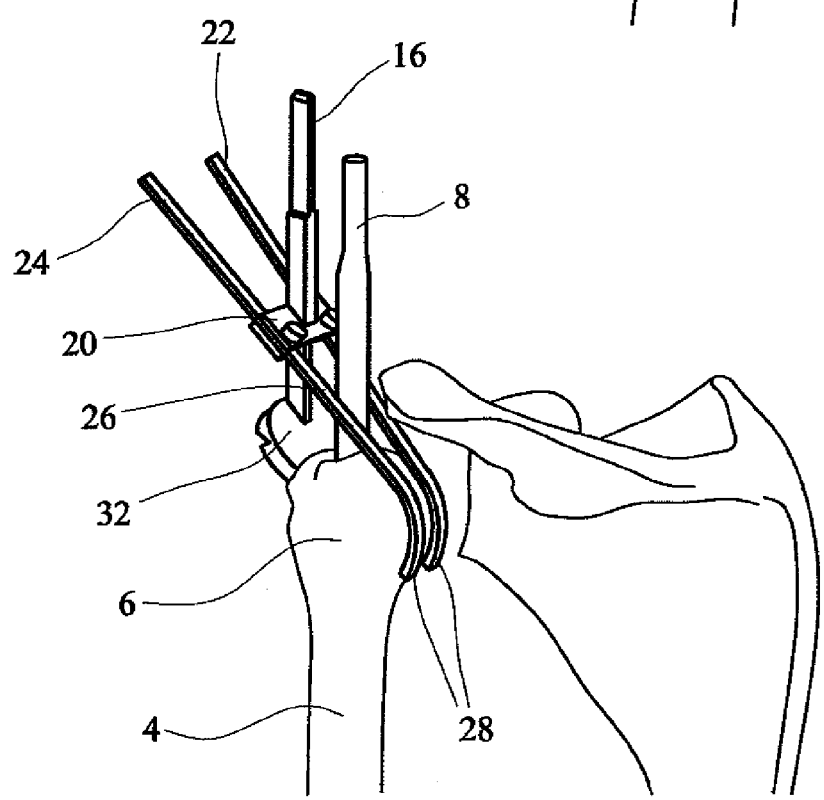
FIG. 2 is a isometric view of the posterior aspect of the shoulder joint and instrument shown in FIG. 1.
Figure 3:
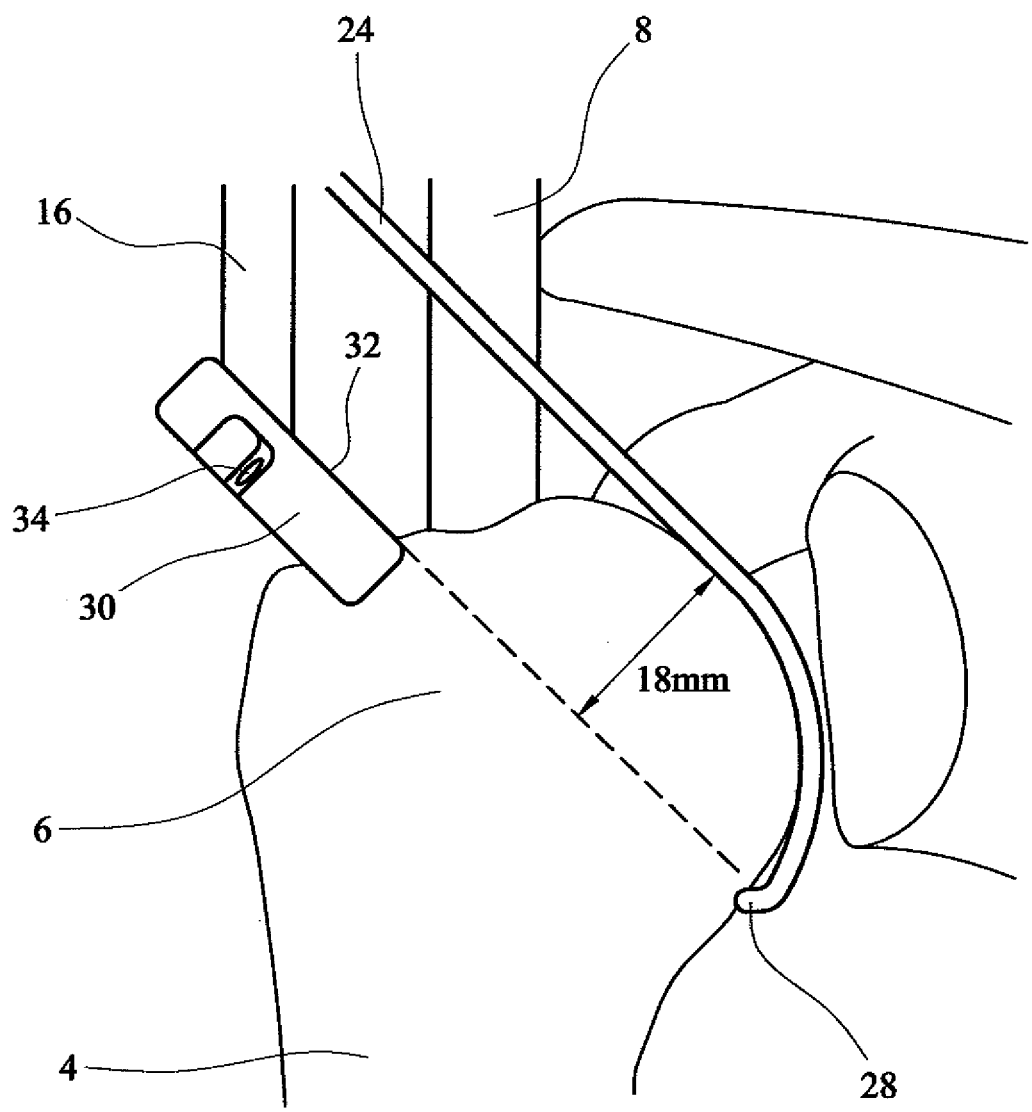
FIG. 3 is an enlarged view of the anterior aspect of head of the humerus, with the instrument of the invention.
Figure 4A:
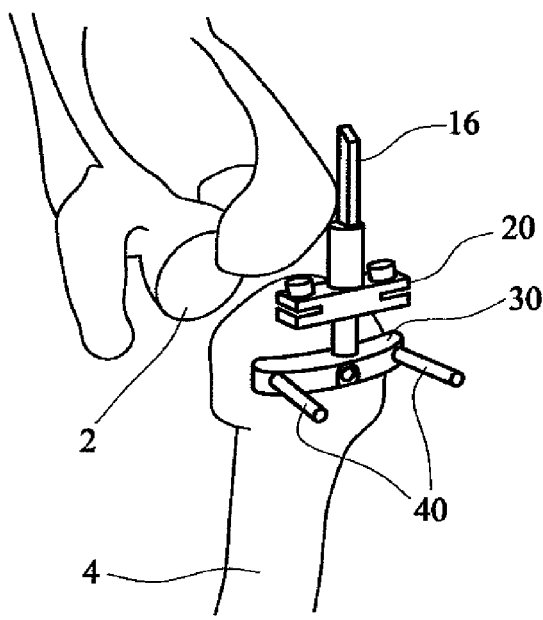
FIGS. 4a to 4d show steps in a surgical procedure to locate the plane for resection of the head of a humerus and to perform the resection. The humerus should be resected on about the plane which marks the edge of the approximately spherical bearing surface on the humerus, which is perpendicular to the polar axis of that bearing surface.

FIGS. 4a to 4d show stages in the procedure for resecting the head of a humerus, after the reference block 30 has been located appropriately relative to the lateral edge of the humerus (as described above with reference to FIGS. 1 to 3). In a first step as shown in FIG. 4a, pins 40 are inserted into the guide holes 34 in the reference block 30, and are tapped using a surgical mallet so that they penetrate the cortical bone of the humerus.

Figure 4B:
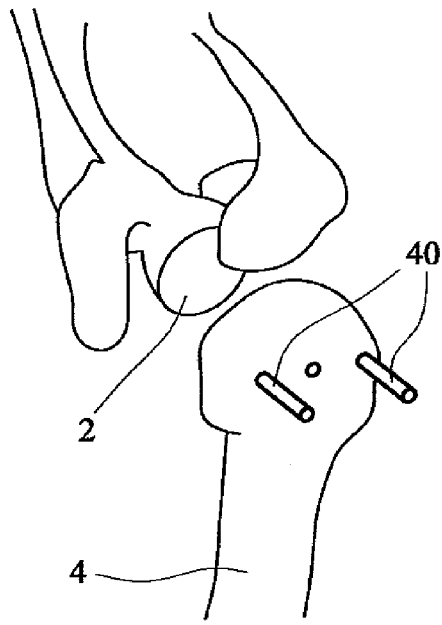

As shown in FIG. 4b, the cutting guide 14, with the reference block 30 and the guide arms 22, 24, is removed from the humerus, which will generally require the removal of some or all of the pins 40 when all of the pins are not parallel to one another. As shown in FIG. 4, two of the pins are parallel to one another. A third central pin which is not parallel to the other two pins should therefore be removed to enable the reference block 30 to be removed from the humerus.

Figure 4C:
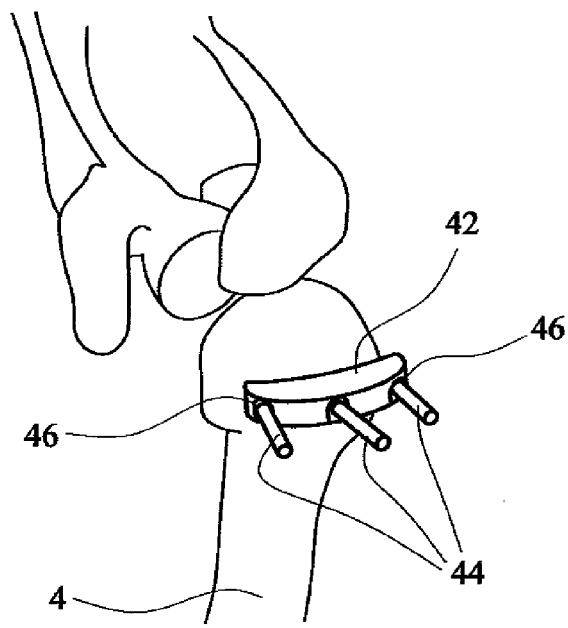

As shown in FIG. 4c, a cutting guide block 42, is fastened relative to the humerus using pins 44 (which might be same pins as those which were tapped into the humerus through the guide holes 34 in the reference block 30) which extend through appropriate fixation holes 46. When the outer two pins are parallel to one another and the central pin is non-parallel, the insertion of the central pin helps to lock the cutting guide block in place against the wall of the humerus.

Figure 4D:
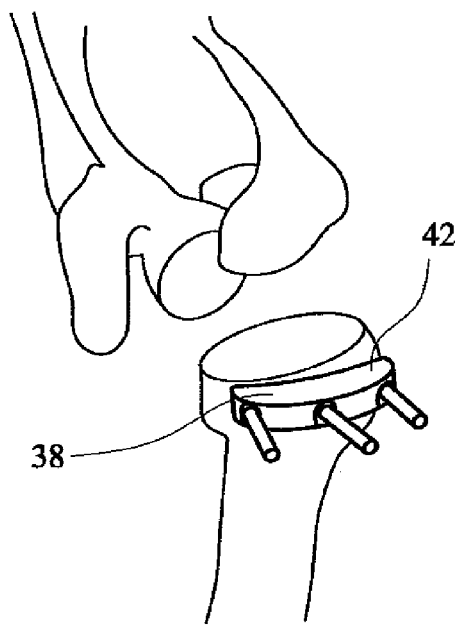

The cutting guide block 42 has a cutting guide surface 48 which can be used to guide the oscillating blade of a saw, to resect the head of the humerus as shown in FIG. 4d.

The invention claimed is:

1. An instrument for locating the cutting plane on the head of a long bone in a surgical procedure wherein the head of the bone is replaced with a joint prosthesis component, the long bone having an axis, comprising:
    an axial reference shaft arranged parallel to the axis of the long bone;
    a cutting guide movable relative to the axial reference shaft in a direction parallel to the axis of the long bone, the cutting guide comprising a reference block configured to be located against the lateral edge of the bone, and at least one arm shaped so that, when the reference block is positioned against the lateral edge of the bone, the at least one arm extends from the cutting guide over the face of the head and contacts the head; and
    wherein the at least one arm has a distal end, and the distal end contacts a medial edge of the bone when the reference block is positioned against the lateral edge of the bone.

2. The instrument of claim 1, wherein the at least one arm has a lip provided on the distal end of the arm and the lip contacts the medial edge of the bone when the reference block is positioned against the lateral edge of the bone.

3. The instrument of claim 1, wherein the at least one arm and the reference block are together moveable relative to the axial reference shaft.

4. The instrument of claim 1, wherein the at least one arm is slidable relative to the cutting guide.

5. The instrument of claim 1, wherein the at least one arm includes an approximately straight portion that extends from the cutting guide and a curved portion that extends from the straight portion towards the medial edge of the bone when the reference block is positioned against the lateral edge of the bone.

6. The instrument of claim 1, wherein the reference block defines a reference block plane and the arm extends from the cutting block in an arm plane that is substantially parallel to the reference block plane, and the distance between the reference block plane and the arm plane is a defined distance.

7. The instrument of claim 6, wherein the defined distance ranges from approximately 15 mm to 21 mm.

8. The instrument of claim 1, wherein the at least one arm is shaped so that, when the reference block is positioned against the lateral edge of the bone, the at least one arm extends from the cutting guide over the face of the head and contacts the superior surface of the head.

9. The instrument of claim 1, further comprising a first arm and a second arm, each of which have a distal end, and wherein the first arm and the second arm are connected to the cutting guide at spaced-apart locations and, when the reference block is positioned against the lateral edge of the bone, each of the first arm and the second arm extends from the cutting guide over the superior face of the head of the bone and at least one distal end of the first and second arm contacts a medial edge of the bone.

10. The instrument of claim 1, further comprising a clamp for locking the cutting guide against movement relative to the axial reference shaft.

11. The instrument of claim 1, wherein the reference block has features that are in or parallel to the intended cutting plane.

12. The instrument of claim 11, wherein the reference block has bores formed therein to define the locations of holes in the long bone to fasten a resection guide block.

13. The instrument of claim 11, wherein the reference block has a surface that corresponds to the cutting plane when the block is properly aligned relative to the head of the bone.

14. The instrument of claim 6, wherein the axial reference shaft is connected on one end to the reference block and is movable relative to the intramedullary element in a direction parallel to the axis of the long bone.

15. The instrument of claim 1, wherein the cutting guide further comprises a mounting block, and wherein the at least one arm is slidably attached to the mounting block in a direction that is not parallel to the axis of the long bone, and the shaft is slidable attached to the mounting block in a direction parallel to the axis of the long bone.

16. An instrument for locating the cutting plane on the head of a long bone in a surgical procedure wherein the head of the bone is replaced with a joint prosthesis component, the long bone having an axis, comprising:
  an axial reference shaft arranged parallel to the axis of the long bone;
  a cutting guide movable relative to the axial reference shaft in a direction parallel to the axis of the long bone, the cutting guide comprising a reference block configured to be located against the lateral edge of the bone, and at least one arm shaped so that, when the reference block is positioned against the lateral edge of the bone, the at least one arm extends from the cutting guide over the face of the head and contacts the head; and
  wherein the reference block defines a reference block plane and the arm extends from the cutting block in an arm plane that is substantially parallel to the reference block plane, and the distance between the reference block plane and the arm plane is a defined distance.

17. The instrument of claim 16, wherein the defined distance ranges from approximately 15 mm to 21 mm.

18. The instrument of claim 16, wherein the axial reference shaft is connected on one end to the reference block and is movable relative to the intramedullary element in a direction parallel to the axis of the long bone.

19. An instrument for locating the cutting plane on the head of a long bone in a surgical procedure wherein the head of the bone is replaced with a joint prosthesis component, the long bone having an axis, comprising:
  an axial reference shaft arranged parallel to the axis of the long bone;
  a cutting guide movable relative to the axial reference shaft in a direction parallel to the axis of the long bone, the cutting guide comprising a reference block configured to be located against the lateral edge of the bone, and at least one arm shaped so that, when the reference block is positioned against the lateral edge of the bone, the at least one arm extends from the cutting guide over the face of the head and contacts the head;
  a first arm and a second arm, each of which have a distal end, and wherein the first arm and the second arm are connected to the cutting guide at spaced-apart locations and, when the reference block is positioned against the lateral edge of the bone, each of the first arm and the second arm extends from the cutting guide over the superior face of the head of the bone and at least one distal end of the first and second arm contacts a medial edge of the bone.

* * * * *